United States Patent [19]

Hara et al.

[11] Patent Number: 5,318,986

[45] Date of Patent: Jun. 7, 1994

[54] METHOD OF INHIBITING THE ACTIVITY OF α-AMYLASE

[75] Inventors: Yukihiko Hara; Miwa Honda, both of Fujieda, Japan

[73] Assignee: Mitsui Norin Co., Ltd., Tokyo, Japan

[21] Appl. No.: 963,263

[22] Filed: Oct. 19, 1992

Related U.S. Application Data

[63] Continuation of Ser. No. 794,820, Nov. 18, 1991, abandoned, which is a continuation of Ser. No. 508,793, Apr. 12, 1990, abandoned.

[30] Foreign Application Priority Data

Oct. 19, 1989 [JP] Japan ................................. 1-270228

[51] Int. Cl.$^5$ ............................................. A61K 31/35
[52] U.S. Cl. ..................................................... 514/456
[58] Field of Search ......................................... 514/456

[56] References Cited

U.S. PATENT DOCUMENTS

| | | | |
|---|---|---|---|
| 4,613,672 | 9/1986 | Hara | 549/399 |
| 4,673,530 | 6/1987 | Hara | 252/398 |
| 4,840,966 | 6/1989 | Hara et al. | 514/456 |

FOREIGN PATENT DOCUMENTS

| | | | |
|---|---|---|---|
| 742073 | 5/1970 | Belgium | 514/456 |
| 1130285 | 6/1986 | Japan | 514/456 |

OTHER PUBLICATIONS

E. Truscheit et al, "Chemistry and Biochemistry of Microbial α-Glucosidase Inhibitors", 1981, pp. 744-761, Angew. Chem. Int. Ed. Engl. 20.

Choi-Lan Ha et al, "In vitro inhibition of trypsin and α-amylase activities by tea", vol. 27, No. 3, Sep. 1989, pp. 406-417-Journal of the Chinese Agriculture Chemical Society.

S. Kashket et al, "Inhibition of Salivary amylase by water-soluble extracts of tea", vol. 33, No. 11, 1988, pp. 845-846-Archives of Oral Biology.

Y. Hara et al, "the inhibition of α-amylase by tea polyphenols", vol. 54, No. 8, aug., 1990, Japan, pp. 1939-1945-Agricultural and Biological Chemistry.

Chakraravarthy et al. 95CA:215159f 1981.

Ha et al. 112 CA:177157p 1989.

Sheehan et al. 99 CA:16374e.

Ohtani et al. CA; 98:155975u 1983.

Horita et al. CA, 89:12190n 1978.

Nakatani et al. CA, 105:197167a 1986.

*Primary Examiner*—Frederick E. Waddell
*Assistant Examiner*—Russell Travers
*Attorney, Agent, or Firm*—Frishauf, Holtz, Goodman & Woodward

[57] ABSTRACT

The effective ingredient in the inventive inhibitive agent against activity of a α-amylase is tea, e.g., black tea, or a tea polyphenol as a constituent of tea including epigallocatechin gallate, epicatechin gallate, epigallocatechin, epicatechin, (+)catechin and the isomer thereof, free theaflavin, theaflavin monogallates A and B and theaflavin digallate.

9 Claims, No Drawings

METHOD OF INHIBITING THE ACTIVITY OF α-AMYLASE

This application is a continuation of application Ser. No. 07/794,820, filed Nov. 18, 1991, (abandoned), which is a continuation of application Ser. No. 07/508,793filed Apr. 12, 1990 (abandoned).

BACKGROUND OF THE INVENTION

1. Field of the Invention

The present invention relates to a novel inhibitive agent against the activity of α-amylase or, more particularly, to an inhibitive agent against the activity of α-amylase with high specificity in the reaction with α-amylase.

2. Background Information

A serious problem in these days called "an age of gluttony" is that many people suffer from corpulence and an adult disease or geriatric disease as a consequence of corpulence so that dieting or control of food intake is an important means for health control. In the midst of this, dietary fibers, which cannot be absorbed as food, are highlighted and utilized in various aspects. The effect of dietary fibers consists in the control of the absorption of harmful substance including carcinogenic ones and enhancement of the evacuating performance of the intestines rather than positive suppression of corpulence.

α-Amylase is a kind of digestive enzyme capable of hydrolyzing polysaccharides and is contained in the saliva and pancreatic juice of humans. Accordingly, inhibition of the activity of α-amylase would hopefully have an effect to prevent corpulence with adequate satisfaction of the appetite and exhibit a therapeutic effect for diabetes. Several inhibitive agents against the activity of α-amylase have been developed with such an object, although none of them is quite satisfactory in the activity with certain undesirable side effects in some of them.

Accordingly, it is advantageous to develop a novel inhibitive agent against the activity of α-amylase which can be administered to patients without undesirable side effects against human body.

SUMMARY OF THE INVENTION

An object of the present invention is to provide a novel inhibitive agent against activity of α-amylase as mentioned above. The inventors have conducted extensive investigations of natural products to discover a substance capable of exhibiting the desired effect without the problems usually encountered in chemically synthesized compounds.

Thus, the inhibitive agent of the present invention against the activity of α-amylase comprises tea as the medicinally effective ingredient.

Further, the inhibitive agent of the invention comprises polyphenol compounds in tea as the effective ingredient. The polyphenol compound in tea as the effective ingredient in the inhibitive agent is selected from the group consisting of epigallocatechin gallate, epicatechin gallate, epigallocatechin, epicatechin, (+) catechin and the isomer thereof, free theaflavin, theaflavin monogallate A, theaflavin monogallate B and theaflavin digallate.

DETAILED DESCRIPTION OF THE PREFERRED EMBODIMENTS

The present invention provides a novel inhibitive agent against the activity of α-amylase, of which tea is the effective ingredient.

The tea polyphenol compounds as the principal effective ingredients in the inventive inhibitive agent against the activity of α-amylase include the tea catechin compounds represented by the general formula (I) given below and the theaflavin compounds represented by the general formula (II) given below:

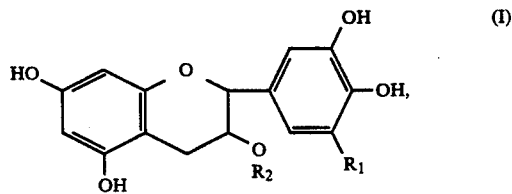

in which $R_1$ is a hydrogen atom or a hydroxy group and $R_2$ is a hydrogen atom or a 3,4,5-trihydroxy benzoyl group; and

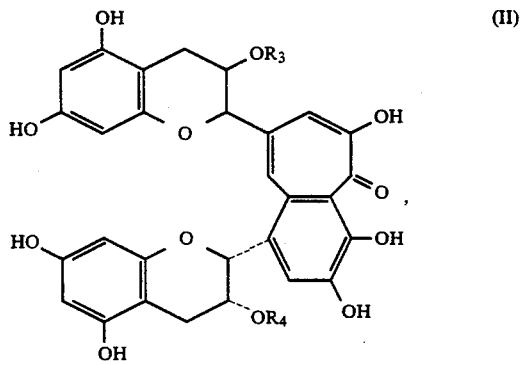

in which $R_3$ and $R_4$ are, each independently from the other, a hydrogen atom or a 3,4,5-trihydroxy benzoyl group. Particular examples of the tea catechin compounds represented by the general formula (I) include: (−)epicatechin, which is a compound of the formula (I) with $R_1$=H and $R_2$=H; (−)epigallocatechin, which is a compound of the formula (I) with $R_1$=OH and $R_2$=H; (−)epicatechin gallate, which is a compound of the formula (I) with $R_1$=H and $R_2$=3,4,5-trihydroxy benzoyl group; and (−)epigallocatechin gallate, which is a compound of the formula (I) with $R_1$=OH and $R_2$=3,4,5-trihydroxy benzoyl group. Particular examples of the theaflavin compounds include: free theaflavin, which is a compound of the formula (II) and $R_3$=H and $R_4$=H; theaflavin monogallate A, which is a compound of the formula (II) with $R_3$=3,4,5-trihydroxy benzoyl group and $R_4$=H; theaflavin monogallate B, which is a compound of the formula (II) with $R_3$=H and $R_4$=3,4,5-trihydroxy benzoyl group; and theaflavin digallate, which is a compound of the formula (II) with $R_3$=3,4,5-trihydroxy benzoyl group and $R_4$=3,4,5-trihydroxy benzoyl group.

The above described tea polyphenol compounds can be prepared from tea leaves as the starting material and a method for the preparation thereof and a typical example of the product composition are described, for example, in Japanese Patent Kokai 59-219384, 60-13780 and 61-130285 and elsewhere.

When the inventive inhibitive agent against the activity of α-amylase is to be processed into a medicament form or as an additive for food etc., the above described tea polyphenol as the effective ingredient as such is admixed with the base without or with dilution with water or alcohol. In this case, the concentration thereof in the digestive tract is preferably in the range from 0.1 µM to 5 mM or, more preferably, form 0.5 µM to 1 mM.

The above described inhibitive agent against activity of α-amylase comprises, as the effective ingredient, a natural product which is in a drinkable form taken in daily life in a considerably large volume so that it is absolutely free from the problem of undesirable side effects against the human body, not only when it is used as a medicine but also when it is used as an additive of food. Moreover, the effectiveness thereof is so high that the activity of α-amylase can be effectively inhibited by the addition thereof even in a very low concentration to provide a means for inhibiting the activity of α-amylase.

In the following, examples are given to illustrate the invention in more detail.

EXAMPLE 1

The enzyme used here was a product of α-amylase prepared from human saliva and supplied by Sigma Co.

A 150 µl of the enzyme solution (0.44 U/ml in a buffer solution) was added to 1230 µl of the sample solution and the mixture was incubated at 37° C. for 10 minutes. Thereafter, the sample solution was admixed with 120 µl of a solution of soluble starch as the substrate so as to have a final concentration of the substrate of 2.0 mg/ml to effect the reaction at 37° C. A 200 µl of the solution was taken in every 3 minutes from the solution under proceeding reaction and the reducing sugar produced therein was determined by the measurement of the absorbance at a wavelength of 540 nm according to the method of Bernfeld described in Meth. Enzymol., volume 1, page 49 (1959) by P. Bernfeld. The value of the absorbance was converted by calculation into the amount of maltose from which the reaction velocity was calculated according to the conventional procedure. The concentration of the solution for 50% inhibition of the activity of α-amylase was determined with each sample assuming that the activity of α-amylase was 100% when the reaction velocity was equal to that in the control in which the same volume of the buffer solution was added in place of the sample solution. The results are shown in Table 1 below.

TABLE 1

| Sample | Concentration for 50% inhibition |
|---|---|
| Gallic acid | >>1 mM |
| Epicatechin | >>1 mM |
| Isomer of epicatechin | >>1 mM |
| Epigallocatechin | >>1 mM |
| Isomer of epigallocatechin | >>1 mM |
| Epicatechin gallate | 130 µM |
| Isomer of epicatechin gallate | 20 µM |
| Epigallocatechin gallate | 260 µM |
| Isomer of epigallocatechin gallate | 55 µM |
| Free theaflavin | 18 µM |
| Theaflavin monogallate A | 1.0 µM |
| Theaflavin monogallate B | 1.7 µM |
| Theaflavin digallate | 0.6 µM |

A conclusion could be derived from the above given results that, among the catechin compounds shown in the table, epicatechin, epigallocatechin and isomers thereof have almost no power for the inhibition of the activity of α-amylase, but the other catechin compounds and theaflavin compounds have a strong power for the inhibition of the activity of α-amylase.

EXAMPLE 2

Each of 12-week old male rats of the Wistar strain, divided into a test group and a control group, was fed a high-carbohydrate diet either with or without, respectively, of 1% by weight of Polyphenon 100 which was a crude mixture of catechin compounds in a proportion shown in Table 2 below.

TABLE 2

| | Polyphenon 100 | |
|---|---|---|
| Catechin compound | Content, % | Relative content, % |
| Gallocatechin | 1.44 | 1.6 |
| Epigallocatechin | 17.57 | 19.3 |
| Catechin | — | — |
| Epicatechin | 5.81 | 6.4 |
| Epigallocatechin gallate | 53.90 | 59.1 |
| Epicatechin gallate | 12.51 | 13.7 |
| Total | 91.23 | 100 |

The formulation of the high-carbohydrate diet given to the control animals was as shown below in Table 3. In the diet given to the test animals, the formulation was modified by decreasing the amount of the starch powder to 70.0% and addition of 1.0% of Polyphenon 100 instead.

TABLE 3

| Constituent | Content in high-carbohydrate diet (control), % | Content in the diet being added Polyphenon 100, % |
|---|---|---|
| Casein | 22.0 | 22.0 |
| Salt mix | 4.0 | 4.0 |
| Corn oil | 2.0 | 2.0 |
| Vitamin complex | 1.0 | 1.0 |
| Starch powder | 71.0 | 70.0 |
| Polyphenone 100 | — | 1.0 |
| Total | 100 | 100 |

After 7 days of feeding in this manner, the feces discharged from each animal was collected for one day and weighed to examine the change in the amount thereof caused by the addition of Polyphenon 100 to the diet. The results were that the amount in the control animals was 1.01 g per day per animal while the amount in the test animals was 1.78 g per day per animal to support the conclusion that the addition of the catechin compounds to the diet was effective to increase the amount of feces discharge. This result means that the catechin compounds act in a similar manner to dietary fibers in promoting the evacuating performance of the intestines by decreasing absorption of the carbohydrates as a consequence of the power to inhibit the activity of amylase.

EXAMPLE 3

When the inventive inhibitive agent against the activity of α-amylase is administrated to the human body, the dose to be taken orally is 0.1 to 10 g per day or, preferably, 2 to 5 g per day. The form of the medicament is not particularly limitative and it can be taken as such or in the form of a powder, tablet, capsule and the like, optionally, with admixture of an extending agent. When the inventive agent is used as an additive in food, it is added to various kinds of processed food and confectionery such as breads, noodles, cakes, biscuits, cookies and the like in an amount of 0.2 to 1.0% by weight.

EXAMPLE 4

An animal test was conducted by using ICR mice as the test animals to examine the acute toxicity of the inventive inhibitive agent against the activity of α-amylase. The values of $LD_{50}$ calculated according to the Van der Waerdrn method within the confidence limit were: 2412 mg/kg in the oral administration of the same crude mixture of catechin compounds as used in Example 2; 55.2 mg/kg in the intraperitoneal administration of a crude mixture of theaflavin compounds of the composition shown in Table 5 below; and 150 mg/kg in the intraperitoneal administration of epigallocatechin gallate.

TABLE 5

| Compound | Content, %, in the crude mixture of theaflavin compounds |
| --- | --- |
| Free theaflavin | 10.0 |
| Theaflavin monogallate A | 22.3 |
| Theaflavin monogallate B | 19.5 |
| Theaflavin digallate | 32.5 |
| (+) Catechin | 0.3 |
| (−) Epicatechin | 1.8 |
| (−) Epigallocatechin gallate | 4.7 |
| Isomer of (−) epigallocatechin gallate | 1.0 |
| (−) Epicatechin gallate | 3.9 |
| Others (isomers of theaflavin, etc.) | 4.0 |

What is claimed is:

1. A method of providing a therapeutic effect for diabetes in a human in need thereof mediated by inhibiting the activity of α-amylase in the digestive tract of said human comprising orally administering to said human in the form of a powder, tablet or capsule 0.3g to 10 g per day of at least one gallated catechin compound or theaflavin compound selected from the group consisting of epigallocatechin gallate, isomer of epigallocatechin gallate, epicatechin gallate, isomer of epicatechin gallate, free theaflavin, theaflavin monogallate A, theaflavin monogallate B and theaflavin digallate.

2. The method of claim 1, wherein said catechin compound is epigallocatechin gallate or an isomer thereof.

3. The method of claim 1, wherein said catechin compound is epicatechin gallate or an isomer thereof.

4. The method for claim 1 wherein the amount of said tea polyphenol which is administered is from 2 to 5g per day.

5. The method of claim 1 wherein the at least one gallated catechin compound or teaflavin compound is administered in admixture with a food and the at least one gallated catechin compound or teaflavin compound is in an amount of 0.2 to 1.0% by weight, based on the weight of said food.

6. The method of claim 1, wherein the theaflavin compound is free theaflavin.

7. The method of claim 1, wherein the theaflavin compound is theaflavin monogallate A.

8. The method of claim 1, wherein the theaflavin compound is theaflavin monogallate B.

9. The method of claim 1, wherein the theaflavin compound is theaflavin digallate.

* * * * *